US00PP32170P2

(12) United States Plant Patent
Jones

(10) Patent No.: US PP32,170 P2
(45) Date of Patent: Sep. 8, 2020

(54) ***LEUCANTHEMUM* 'LBEWH06-0'**

(50) Latin Name: *Leucanthemum hybrida*
Varietal Denomination: LBEWH06-0

(71) Applicant: Steve Jones, Santa Monica, CA (US)

(72) Inventor: Steve Jones, Santa Monica, CA (US)

( * ) Notice: Subject to any disclaimer, the term of this patent is extended or adjusted under 35 U.S.C. 154(b) by 23 days.

(21) Appl. No.: 16/501,571

(22) Filed: Apr. 30, 2019

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./263.1, 284, 285
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Leucanthemum* hybrid cultivar named 'LBEWH06-0' is disclosed, characterized by a uniquely very large single inflorescence. Plants are overall low growing, compact and tolerate low temperatures to USDA Zone 4. The new variety is a *Leucanthemum* hybrid, typically used for ornamental outdoor purposes.

2 Drawing Sheets

Latin name of the genus and species: *Leucanthemum hybrida.*

Variety denomination: 'LBEWH06-0'.

BACKGROUND OF THE INVENTION

The new cultivar was selected from a mass planting of proprietary seedlings by the inventor, Steve Jones. The parent varieties are unidentified, as the variety resulted from an open pollination and mass collected seed from breeding blocks including several varieties of *Leucanthemum* plants. The open pollination crossing was made during September of 2016. The new variety was selected during April 2017 at a research greenhouse in Santa Paula, Calif.

Asexual reproduction of the new cultivar 'LBEWH06-0' by vegetative cuttings was first performed in May 2017, at a commercial greenhouse in Santa Paula, Calif. All subsequent propagation has shown that the unique features of this cultivar are stable and reproduced true to type in successive generations.

SUMMARY OF THE INVENTION

The cultivar has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LBEWH06-0' These characteristics in combination distinguish 'LBEWH06-0' as a new and distinct *Leucanthemum* cultivar:

1. Very large inflorescence.
2. Day-lenth neutral.
3. Compact plant with a mature height around 50 cm.
4. Cold hardy to Zone 4.

PARENT COMPARISON

The exact parent varieties cannot be identified.

COMMERCIAL COMPARISON

Plants of the new cultivar 'LBEWH06-0' are similar to plants of the commercial variety *Leucanthemum* 'Angel Daisy', unpatented, in most horticultural characteristics. However, plants of the new cultivar 'LBEWH06-0' differ in the following characteristics;

1. 'LBEWH06-0' has a single inflorescence form, whereas 'Angel Daisy' has a somewhat anemone type inflorescence.
2. Inflorescence of 'LBEWH06-0' have a larger diameter than those of 'Angel Daisy'.
3. Plants of 'LBEWH06-0' are cold hardy to Zone 4, plants of 'Angel Daisy' are cold hardy to Zone 6.

Plants of the new cultivar 'LBEWH06-0' are also similar to plants of the commercial variety *Leucanthemum* 'LWMWH03-0', U.S. Plant Pat. No. 23,151, in most horticultural characteristics. However, plants of the new cultivar 'LBEWH06-0' differ in the following characteristics;

1. Inflorescences 'LBEWH06-0' are approximately double in diameter compared to those of 'LWMWH03-0'.
2. Plants of 'LBEWH06-0' have a more compact plant habit than 'LWMWH03-0'.
3. Plants of 'LBEWH06-0' are shorter than plants of 'LWMWH03-0'.

BRIEF DESCRIPTION OF THE PHOTOGRAPHS

Figure 1:
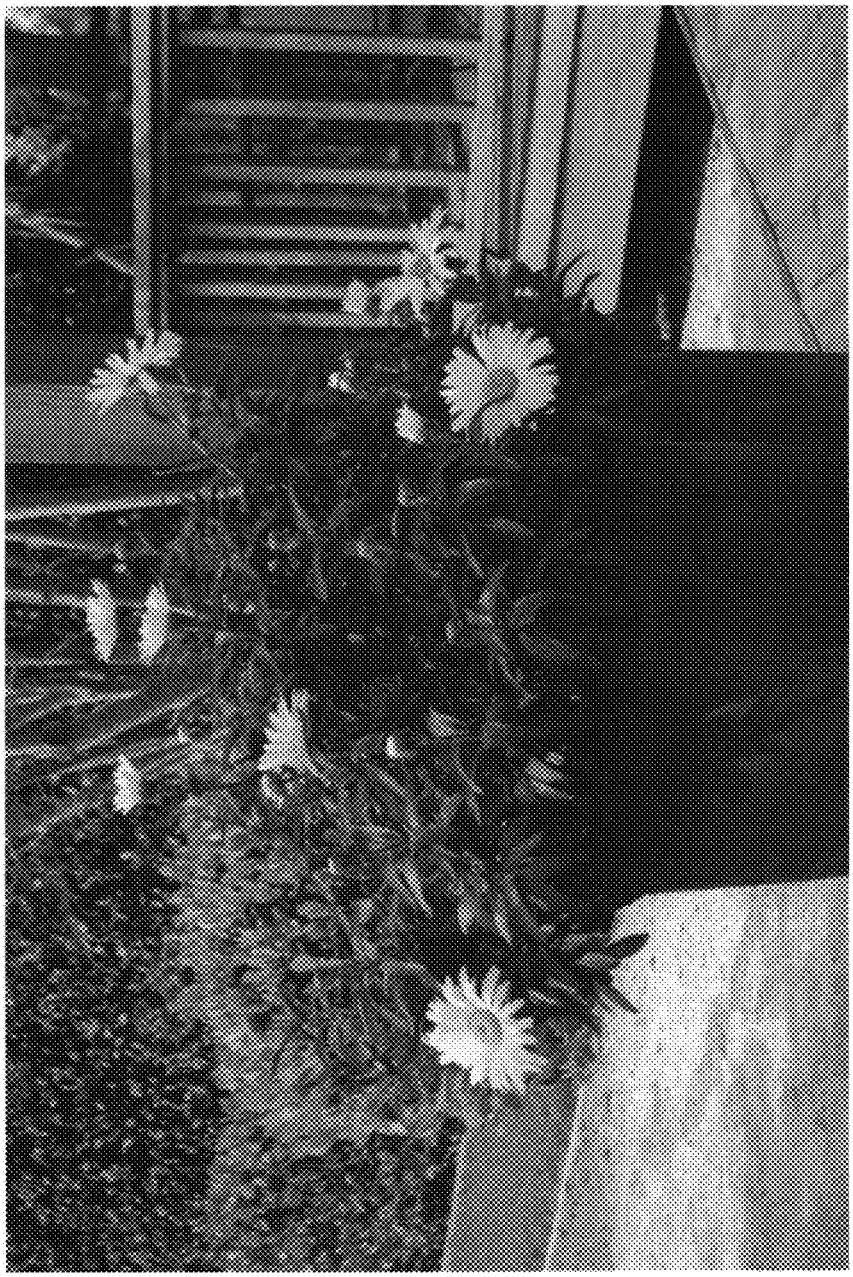

The accompanying photograph in FIG. 1 illustrates in full color typical plants of 'LBEWH06-0' grown in Santa Paula, Calif. The plants shown are approximately 20 weeks old in a 30 cm pot.

Figure 2:
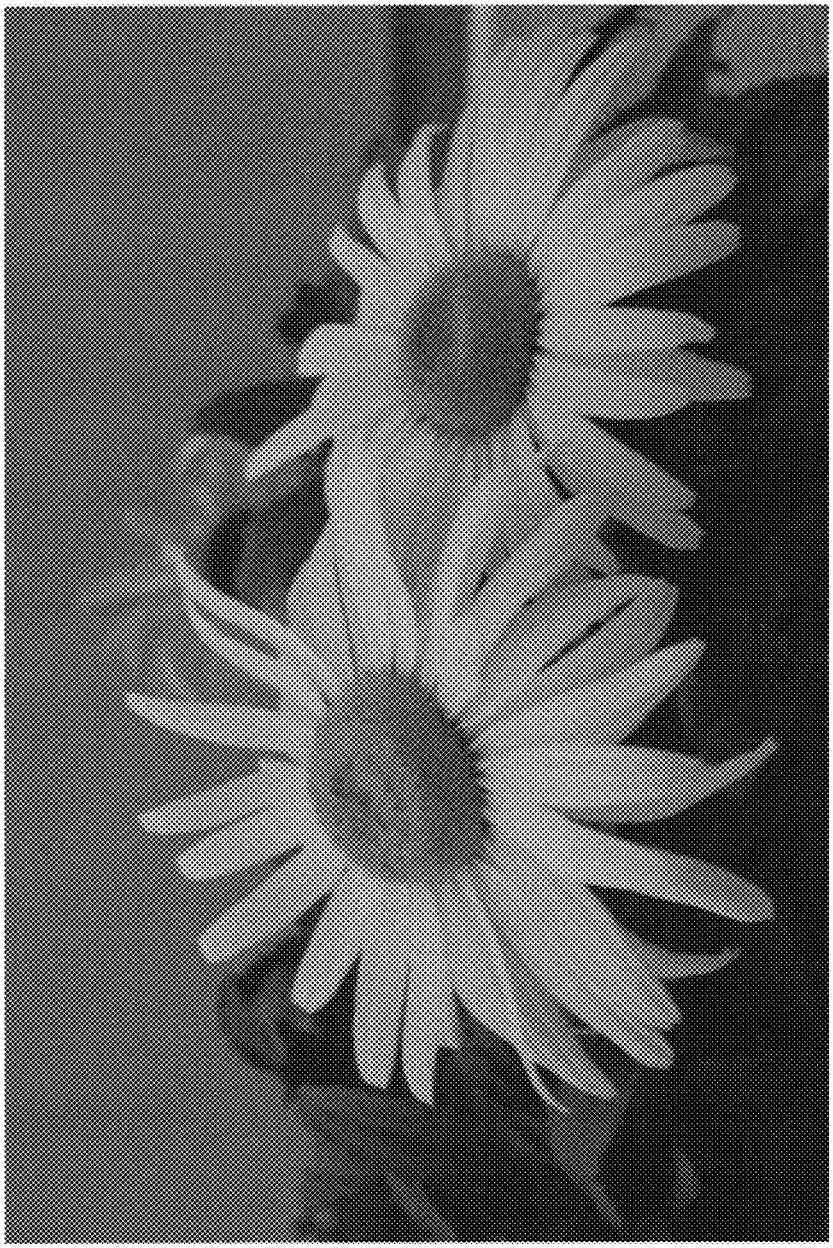

FIG. 2 illustrates a close up view of the inflorescence.

The photographs were taken using conventional techniques and although colors may appear different from actual colors due to light reflectance it is as accurate as possible by conventional photographic techniques.

In the following description, color references are made to The Royal Horticultural Society Colour Chart, 2007 except where general terms of ordinary dictionary significance are used. The following observations and measurements describe 'LBEWH06-0' plants grown in a greenhouse in Santa Paula, Calif. from Fall to Spring. The growing temperature ranged from 15° C. to 16° C. at night to 15° C. to 32° C. during the day. Measurements and numerical values represent averages of typical flowering types.

Botanical classification: *Leucanthemum superbum* 'LBEWH06-0'.

PROPAGATION

Time to rooting: Approximately 20 days at approximately 20° C.

Root description: Fine, fibrous. Brown roots not accurately measured with an R.H.S. chart.

PLANT

Pot size: 1 gallon.

Height: Approximately 23 cm to top of foliar plane. Approximately 27 cm to top of the highest flower.

Plant spread: Approximately 28 cm.

Growth rate: Moderate.

Branching characteristics: Moderately free branching.

Length of lateral branches: Average range 10 to 18 cm.

Diameter of lateral branches: Approximately 0.6 cm.

Quantity of lateral branches: Approximately 2 to 3 per main branch.

Texture of lateral branches: Slightly pubescent, ridged stem.

Color of lateral branches: Near RHS Green 137A.

Aspect: Straight.

Internode length: Average range 10 to 15 mm.

Average number of leaves per lateral branch: Approximately 16 to 20.

Age of plant described: Approximately 24 weeks from an unrooted cutting.

FOLIAGE

Leaf:

*Arrangement*.—Alternate, simple.

*Average length*.—Average range 7.8 to 10.5 cm.

*Average width*.—Approximately 2.9 cm.

*Shape of blade*.—Oblanceolate.

*Apex*.—Acute.

*Base*.—Truncate.

*Attachment*.—Sessile.

*Margin*.—Dentate.

*Texture of top surface*.—Smooth.

*Texture of bottom surface*.—Smooth. Pubescent along mid-vein.

*Leaf internode length*.—Average range 5 to 9 mm.

*Color*.—Young foliage upper side: Near RHS Green 137A. Young foliage under side: Near RHS Green 137B. Mature foliage upper side: Near RHS Green 139A. Mature foliage under side: Near RHS Green 137B.

*Venation*.—Type: Pinnate. Venation color upper side: Near RHS Yellow-Green 144B. Venation color under side: Near RHS Green 143C.

FLOWER

Bloom period: Naturally blooming from Spring to early Fall.

Bud:

*Bud shape*.—Flattened sphere.

*Bud length*.—Approximately 0.8 cm.

*Bud diameter*.—Approximately 1.7 cm.

*Bud color*.—Near RHS Green 137A.

Inflorescence:

*Quantity per plant*.—Average range around 5 open inflorescence on a plant in a 1 gallon pot.

*Form*.—Simple composite daisy. Inflorescences occurring mainly on upright terminal peduncles, pinching promotes flowering on lateral peduncles.

*Lastingness of inflorescence*.—Approximately 1 weeks to 3 weeks in good condition, from fully opened, depending upon environmental conditions.

Inflorescence:

*Diameter of entire inflorescence*.—Average range 12 to 17 cm.

*Depth of inflorescence*.—Approximately 2 cm.

*Width of disc*.—Approximately 3.7 cm.

*Depth of disc*.—Approximately 1.1 cm.

*Receptacle*.—Shape: Flattened. Width: 2.5 cm. Depth: 0.6 mm. Color: Near RHS Yellow-Green 145C.

Ray florets:

*Number of ray florets*.—Average range 35 to 45 in 2 to 3 whorls.

*Length*.—Average 4 to 5 cm.

*Width*.—Approximately 0.6 cm.

*Apex*.—3 narrow, rounded lobes.

*Base*.—Attenuate.

*Shape*.—Oblanceolate.

*Margin*.—Entire.

*Texture*.—Smooth all surfaces.

*Aspect*.—Slightly reflexing.

Color:

*Ray floret*.—Upper surface at first opening: Near RHS White 155B, small basal section colored Yellow-Green 144A. Upper surface at maturity: Near RHS White 155A small basal section colored Green 143C. Upper surface at fading: Near RHS White 155B, small basal section colored Yellow-Green 144A. Under surface at first opening: Near RHS White 155D, small basal section colored Green 143B. Under surface at maturity: Near RHS White 155B small basal section colored Green 143C. Under surface at fading: Near RHS White 155B, small basal section colored Yellow-Green 144B.

*Disc florets*.—Number: About 500. Length: Average 7 to 8 mm. Width: Base about 1.0 mm, apex can flare to 2 mm wide. Apex: 3 to 4 lobes, blunt rounded. Shape: Cylindric, opening at apex to 4 flared lobes. Margin: Entire.

Color:

*At first opening*.—Base near RHS Yellow-Green 145A, apex near Yellow 11A.

*At maturity*.—Base near RHS Yellow-Green 145B, apex near Yellow-Orange 14B.

*At fading*.—Base near RHS Yellow-Green 145B, apex near Yellow-Orange 14C.

Fragrance: Moderate to faint musty scent.

Involucral bracts/phyllaries:

Number: Approximately 50 in 2 to 3 tightly held rows.

Length: Approximately 7 to 10 mm.

Width: Approximately 3 to 4 mm.

Shape: Oblong.

Apex: Broad acute.

Base: Truncate.

Margin: Entire, membranous.
Texture: Glabrous.
Color: Inside surface color near RHS Green 137C, with margin colored Green 138C. Outside surface near Green 137A with margin colored Green 138B.
Peduncle:
Length: Average 4 cm.
Width: Approximately 5 mm.
Texture: Ridged.
Color: Near RHS Green 137A.

REPRODUCTIVE ORGANS

Androecium: Present on disc florets only.
*Stamens*.—4.
*Anther length*.—Approximately 0.5 mm.
*Anther color*.—Near RHS Yellow-Orange 22A.
*Pollen color*.—Scant colored near RHS Yellow-Orange 14B.
Gynoecium: Present on ray and disc florets.
Ray florets:
Number of pistils per flower: 1.
*Pistil length*.—About 5 mm.
*Stigma shape*.—Two parted.
*Stigma color*.—Near RHS Greyed-Orange 166A.
*Style color*.—Near RHS White 155D.
*Style length*.—Approximately 3 mm.
Disc florets:
Number of pistils per flower: 1.
*Stigma shape*.—Two parted.
*Stigma color*.—Near RHS Yellow-Orange 22A.
*Style color*.—Near RHS Green-Yellow 1B.
*Style length*.—Approximately 2 mm.

OTHER CHARACTERISTICS

Disease and pest resistance: Neither resistance nor susceptibility to diseases or pests has been observed in this variety to date.
Temperature tolerance: Hardy perennial. Hardy to at least −2° C., high temperature tolerance to at least 35° C.
Fruit/seed production: Fruit and seed production have not been observed in the new cultivar.

What is claimed is:

1. A new and distinct cultivar of *Leucanthemum* plant named 'LBEWH06-0' as herein illustrated and described.

* * * * *